United States Patent [19]
Berner et al.

[11] Patent Number: 5,306,829
[45] Date of Patent: Apr. 26, 1994

[54] UV ABSORBERS AND LIGHT-SENSITIVE ORGANIC MATERIAL CONTAINING SAME

[75] Inventors: Godwin Berner, Binningen, Switzerland; Andreas Valet, Eimeldingen, Fed. Rep. of Germany

[73] Assignee: Ciba-Geigy Corporation, Ardsley, N.Y.

[21] Appl. No.: 919,664

[22] Filed: Jul. 24, 1992

Related U.S. Application Data

[63] Continuation of Ser. No. 836,141, Feb. 13, 1992, abandoned, which is a continuation of Ser. No. 628,733, Dec. 17, 1990, abandoned.

[30] Foreign Application Priority Data

Dec. 21, 1989 [CH] Switzerland ............... 4579/89-4

[51] Int. Cl.$^5$ ............................................. C07D 311/82
[52] U.S. Cl. ................................................. 549/223
[58] Field of Search ........................ 546/103; 549/223

[56] References Cited

U.S. PATENT DOCUMENTS

| | | | |
|---|---|---|---|
| 3,624,087 | 11/1971 | Beck | 260/279 |
| 3,728,350 | 4/1973 | Beck | 260/287 |
| 3,732,204 | 5/1973 | Beck | 260/279 |
| 3,766,187 | 10/1973 | Beck | 260/279 |
| 4,266,020 | 5/1981 | Sakgi et al. | 430/551 |
| 4,691,059 | 4/1987 | Mitra et al. | 546/103 |

FOREIGN PATENT DOCUMENTS 924019 4/1963 United Kingdom ............... 400/551

OTHER PUBLICATIONS

G. S. Puranik et al., Monatsheffe Chem., 94, 410 (1963).
Chem. Abst. 110, 31366t (1989).
G. S. Puranik et al., Indian J. Chem., 19, 1157 (1972).
V. M. Chari et al., Helv. Chem. Acta. 62, 678 (1979).
R. R. Smolders et al., Bull. Soc. Chim., Belg. 93, 239 (1984).
J. Hlubucek et al., Aust. J. Chem. 23, 1881 (1970).
A. C. Jain et al., Tetrahedron, 25, 275 (1969).

*Primary Examiner*—C. Warren Ivy
*Assistant Examiner*—Raymond Covington
*Attorney, Agent, or Firm*—William A. Teoli, Jr.

[57] ABSTRACT

A compound of formula

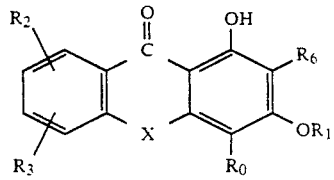

wherein $R_0$, $R_1$, $R_2$, $R_3$, $R_6$ and X are as defined in claim 1, are suitable for use as UV absorbers for protecting light-sensitive organic materials.

4 Claims, No Drawings

UV ABSORBERS AND LIGHT-SENSITIVE ORGANIC MATERIAL CONTAINING SAME

This is a continuation of Ser. No. 836,141 filed Feb. 13, 1992, non abandoned, which is a continuation of Ser. No. 628,733 filed Dec. 17, 1990, now abandoned.

The present invention relates to novel UV absorbers of the anthrone, acridone and xanthone type, and to light-sensitive organic material containing same.

A process for protecting light-sensitive materials from the harmful influence of light, especially of UV rays, in which 1-hydroxyanthraquinones are used, is disclosed in CH-A-379 760.

It has now been found that certain anthrones, acridones and a further class of xanthone compounds can be successfully used for this purpose.

Specifically, the invention relates to compounds of formula $$\text{(1)}$$

wherein X is O, NH or $CH_2$ and $R_0$ is hydrogen or a radical of formula $-(CH_2)_nCO_2R$, wherein n is 1 or 2 and R is alkyl of 1 to 18 carbon atoms or $-(CH_2CH_2O)_m H$, wherein m is 1 to 12, $R_1$ is alkyl of 1 to 18 carbon atoms or alkyl of 4 to 18 carbon atoms which is substituted by hydroxyl and/or may be interrupted by oxygen atoms, or is $-COR_4$, wherein $R_4$ is alkyl or alkenyl, each of 2 to 12 carbon atoms, $$-(CH_2)_y-\overset{O}{\underset{\|}{C}}R_5 \quad \text{or} \quad -OCH_2CH(OH)CH_2O-\overset{O}{\underset{\|}{C}}R_5,$$

or $R_1$ is $$-(CH_2)_y O-\overset{O}{\underset{\|}{C}}R_5 \quad \text{or} \quad -(CH_2)_y \overset{O}{\underset{\|}{C}}OR_5,$$

wherein $R_5$ is alkyl of 1 to 12 carbon atoms or alkenyl of 2 to 12 carbon atoms, and y is 1 to 12, and $R_2$ and $R_3$ are each independently of the other hydrogen, alkyl of 1 to 12 carbon atoms, alkenyl of 2 to 12 carbon atoms, $-OR_1$, wherein $R_1$ has the given meaning, or are chloro, and $R_6$ is hydrogen or alkyl of 1 to 4 carbon atoms.

The invention also relates to a process for the preparation of these compounds, to light-sensitive organic material which contains at least one of said compounds, wherein X is O, as well as to a method of protecting light-sensitive organic materials by using the compounds of formula (1), wherein X is O.

In the compounds of formula (1), the substituent $R_0$ is, in addition to hydrogen, a radical of formula $-(CH_2)_n-CO_2R$. In this formula, R is an alkyl radical of 1 to 18 carbon atoms such as methyl, ethyl, propyl, butyl, hexyl, octyl, decyl, undecyl, dodecyl, hexadecyl and octadecyl, and corresponding branched isomers, or is a radical of formula $-(CH_2CH_2O)_m H$, wherein m is an integer from 1 to 12. The index n is 1 or 2. $R_1$ is alkyl of 1 to 18 carbon atoms, i.e. typically methyl, ethyl, propyl, butyl, pentyl, hexyl, octyl, decyl, dodecyl, hexadecyl or octadecyl, and may also suitably be corresponding branched alkyl radicals. The alkyl radicals $R_1$, if they contain 4 to 18 carbon atoms, may be substituted by one or more hydroxyl groups. They may also be interrupted by one or more oxygen atoms and may additionally contain one or more hydroxyl groups. Illustrative examples of such alkyl radicals are groups such as $-(CH_2)_x-O-(CH_2)_y H$ and $-(CH_2)_x-O-(CH_2)_y-O-(CH_2)_z H$, wherein the sum of x and y or x, y and z is 4 to 18, and $$-CH_2\underset{\underset{OH}{|}}{CH}CH_2(O)_r(CH_2)_s H,$$

wherein r is 0 or 1 and s is 1 to 15.

$R_1$ is also a radical of formula $-COR_4$, wherein $R_4$ is alkyl or alkenyl each of 2 to 12 carbon atoms. Exemplary of such alkyl radicals are those cited above. Exemplary of alkenyl radicals are ethenyl, propenyl, butenyl, hexenyl, octenyl, nonenyl and dodecenyl. The alkenyl radicals $R_1$ may also be polyunsaturated. $R_1$ may also denote the corresponding branched isomers. $R_4$ also denotes the radicals of formulae $$-(CH_2)_y-\overset{O}{\underset{\|}{C}}R_5 \quad \text{and} \quad -OCH_2CH(OH)CH_2O-\overset{O}{\underset{\|}{C}}R_5.$$

wherein $R_5$ is alkyl of 1 to 12 carbon atoms or alkenyl of 2 to 12 carbon atoms (examples of which are cited above) and y is 1 to 12.

$R_1$ is furthermore a radical of formula $$-(CH_2)_y O-\overset{O}{\underset{\|}{C}}R_5 \quad \text{or} \quad -(CH_2)_y \overset{O}{\underset{\|}{C}}OR_5.$$

wherein $R_5$ and y have the given meanings.

The substituents $R_2$ and $R_3$ are each independently of the other hydrogen, alkyl of 1 to 12 carbon atoms or alkenyl of 2 to 12 carbon atoms (examples of which are cited above), wherein $R_1$ has the given meaning, or chloro.

X is a divalent radical and is $CH_2$, NH or O.

In the compounds of formula (1), the substituents $R_2$ and $R_3$ are preferably hydrogen or methyl.

A further group of preferred compounds of formula (1) comprises those compounds wherein $R_1$ is alkyl of 4 to 12 carbon atoms which may be substituted by hydroxyl and/or interrupted by oxygen, or is $-COR_4$ or $$-(CH_2)_y \overset{O}{\underset{\|}{C}}OR_5.$$

wherein $R_4$ is alkyl of 4 to 8 carbon atoms, y is 1 to 4, and $R_5$ is alkyl of 1 to 4 carbon atoms.

Among these compounds, those compounds are particularly preferred wherein $R_1$ is alkyl of 1 to 8 carbon atoms Further preferred compounds of formula (1) are those wherein $R_0$ is a radical of formula $-CH_2CH_2CO_2R$, wherein R is alkyl of 1 to 8 carbon atoms or $-(CH_2CH_2O)_m H$ and m is 6 to 8. Light-sensitive organic materials can be protected in the practice of this invention from the harmful influence of UV radiation by providing said materials with a protective coating, for example a paint or varnish composition, which contains at least one compound of formula (1), wherein X is O, or by incorporating such a compound in conventional manner in said organic material. In like manner, it is possible to use compounds of formula (1), wherein X is NH or CH$_2$.

Light-sensitive organic materials are, in the practice of this invention, free from sterically hindered amines or hydroxyphenylbenzotriazole derivatives.

Ilustrative examples of light-sensitive organic materials which can be protected in the practice of this invention from the harmful influence of light are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), for example high density polyethylene (HDPE), low density polyethylene (LDPE and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers linear low density polyethylene (LLDPE) and mixtures thereof with low density polyethylene (LDPE), propylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned in 1) above, for example polypropylene/ethylene propylene copolymers, LDPE/EVA, LDPE/EAA, LLDPE/EVA and LLDPE/EAA.

3a. Hydrocarbon resins (for example C$_5$–C$_9$), including hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, for example styrene/[ch-]butadiene, styrene/acrylonitrile, styrene/alkylmethacrylate, styrene/butadiene/alkylacrylate, styrene/maleic anhydride, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or α-methylstyrene, for example styrene on polybutadiene, styrene on polybutadiene/styrene or polybutadiene/acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyalkylacrylates or polyalkylmethacrylates, styrene and acrylonitrile on acrylate/butadiene copolymers, as well as mixtures thereof with the copolymers listed under 5), for example the copolymer mixtures known as ABS, MBS, ASA or AES polymers.

7. Halogenated polymers such as polychloroprene, chlorinated rubbers, chlorinated or sulfochlorinated polyethylene, copolymers of ethylene and chlorinated ethylene, epichlorohydrin homo- and copolymers, preferably polymers of halogenated vinyl compounds, for example poly- vinylchloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from α,β-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkylacrylate copolymers, acrylonitrile/alkoxyalkylacrylate or acrylonitrile/vinyl halide copolymers or acrylonitrile/alkylmethacrylate/butadiene terpolymers.

10. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinylbutyrate, polyallyl phthalate or polyallylmelamine; as well as their copolymers with the olefins mentioned in 1) above.

11. Homopolymers and copolymers of cyclic ethers such as polyalkylene glycols. polyethylene oxide, polypropylene oxide or copolymers thereof with bisglycidyl ethers.

12. Polyacetals such as polyoxymethylene and those polyoxymethylenes which contain ethylene oxide as a comonomer; polyacetals modified with thermoplastic polyurethanes, acrylates or MBS.

13. Polyphenylene oxides and sulfides and mixtures thereof with polystyrene or polyamides.

14. Polyurethanes which are derived from polyethers, polyesters or polybutadienes carrying terminal hydroxyl groups on the one hand and aliphatic or aromatic polyisocyanates on the other, as well as precursors thereof.

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9. 6/12 and 4/6, polyamide 11, polyamide 12, aromatic polyamides obtained by condensation of m-xylene, diamine and adipic acid; polyamides prepared from hexamethylenediamine and isophthalic and/or terephthalic acid, with or without an elastomer a modifier, for example poly-2,4,4-trimethylhexamethylene terephthalamide or poly-m-phenylene isophthalamide; block copolymers of the aforementioned polyamides with polyolefins, olefin copolymers, ionomers or chemically bonded or grafted elastomers; or with polyethers, for example with polyethylene glycol, polypropylene glycol or polytetramethylene glycol; and also polyamides or copolyamides modified with EPDM or ABS, and polyamides condensed during processing (RIM polyamide systems).

16. Polyureas, polyimides and polyamide-imides and polybenzimidazoles.

17. Polyesters derived from dicarboxylic acids and diols and/or from hydroxycarboxylic acids or the corresponding lactones, such as poly-ethylene terephthalate, polybutylene terephthalate, poly-1,4-dimethylolcyclohexane terephthalate, polyhydroxybenzoates as well as block-copolyether esters derived from hydroxyl-terminated polyethers; and also polyesters modified with polycarbonates or MBS.

18. Polycarbonates and polyester carbonates.

19. Polysulfones, polyether sulfones and polyether ketones.

20. Crosslinked polymers which are derived from aldehydes on the one hand and phenols, ureas and melamines on the other hand, such as phenol/formaldehyde resins, urea/formaldehyde resins and melamine/formaldehyde resin.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Crosslinkable acrylic resins derived from substituted acrylic esters such as epoxy acrylates, urethane acrylates or polyester acrylates.

24. Alkyd resins, polyester resins or acrylate resins which are cross-linked with melamine resins, urea resins, polyisocyanates or epoxy resins.

25. Crosslinked epoxy resins which are derived from polyepoxides, for example from bisglycidyl ethers or from cycloaliphatic diepoxides.

26. Natural polymers such as cellulose, rubber, gelatine and chemically modified homologous derivatives thereof such as cellulose acetates, cellulose propionates and cellulose butyrates, or the cellulose ethers, such as methylcellulose; as well as rosins and their derivatives.

27. Mixtures (polyblends) of the aforementioned polymers, for example PP/EPDM, Polyamide 6/EPDM or ABS, PVC/EVA, PVS/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

In addition to containing the compounds of formula (1), the the light-sensitive organic materials may also contain further conventional stabilisers and additives, for example:

1. ANTIOXIDANTS 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example, 2,6-di-tert-butyl-4-methoxyphenol, 2,5-di-tert-butylhydroquinone, 2,5-di-tert-amylhydroquinone. 2,6-diphenyl-4-octadecyloxyphenol.

1.3. Hydroxylated thiodiphenyl ethers, for example, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(4-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-bis(tert-butyl-4-hydroxybenzylmercaptoacetate), bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example 4-hydroxylauranilide, 4-hydroxystearanilide, 2,4-bis(octylmercapto)-6-(3,5-di-tert-butyl-4-hydroxyanilino)-s-triazine, octyl N-(3,5-di-tert-butyl-4-hydroxyphenyl)carbamate.

1.7. Esters of β-(3,5-di-tert-butyl-4-hydroxyphenyl)-propionic acid with mono- or polyhydric alcohols, e.g. with methanol, octadecanol, 1,6-hexanediol, neopentyl glycol, triethylene glycol, pentaerythritol, tri(hydroxyethyl) isocyanurate, thiodiethylene glycol, N,N'-bis(-hydroxyethyl)oxalodiamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalodiamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalodiamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)- trimethylenediamine, N,N'-bis(3,5-di-tert-butyl-4-hydroxyphenylpropionyl)hydrazine.

2. UV ABSORBERS AND LIGHT STABILISERS 2.2. 2-Hydroxybenzophenones, for example the 4-hydroxy, 4-methoxy, 4-octoxy, 4-decyloxy, 4-dodecyloxy, 4-benzyloxy, 4,2', 4'-trihydroxy and 2'-hydroxy-4,4'-dimethoxy derivative.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)-resorcinol, benzoylresorcinol, 2,4-di-tert-butylphenyl 3,5-di-tert-butyl-4-hydroxy-benzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzyl-phosphonic acid monoalkyl esters, e.g. of the methyl or ethyl ester, nickel complexes of ketoximes, e.g. of 2-hydroxy-4-methyl-phenyl undecyl ketoneoxime, nickel complexes of 1-phenyl-4-lauroyl-5-hydroxypyrazole, with or without additional ligands.

2.6. Oxalyl diamides, for example 4,4'-dioctyloxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxalamide, 2-ethoxy-5-tert-butyl-2°-ethyloxanilide and its mixture with 2-ethoxy-2'-ethyl-5,4'-di-tert-butoxanilide and mixtures of ortho-and para-methoxy-disubstituted oxanilides and mixtures of o-and p-ethoxydisubstituted oxanilides.

2.7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxy-phenyl)-4,6-bis(2,4-dimethylphenyl)-1,3,5-triazine, 2-(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalyl diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tertbutylphenyl) pentaerythritol diphosphite, tristearyl sorbitol triphosphite, tetrakis-(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in conjunction with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium stearate, sodium ricinoleate and potassium palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, fluorescent whitening agents, flameproofing agents, antistatic agents and blowing agents.

Among the organic materials which can be protected in the practice of this invention from light-induced degradation, organic polymers are to be singled out for special mention. preferably synthetic polymers. It is therefore preferred to protect thermoplastic polymers and, more particularly, surface-coating compositions in which the polymer binder will preferably be stabilised against the influence of light.

Surface-coating compositions, i.e. paint or varnish compositions, which contain the compounds of formula I may be, for example, pigmented or unpigmented paint or varnish compositions or metallic paints. They may contain an organic solvent or be solvent-free, or they may be water-based paints.

The paint or varnish compositions may contain as binder a polymer selected from those cited previously. Illustrative examples of paint or varnish compositions containing special binders are the following:

1. paint or varnish compositions based on cold- or hot-crosslinkable alkyd, acrylate, polyester, epoxy or melamine resins or mixtures of said resins, to which an optional acid curing catalyst is added;

2. two-component polyurethane paint or varnish compositions based on hydroxylated acrylate, polyester or polyether resins and aliphatic or aromatic polyisocyanates;

3. single component polyurethane paint or varnish compositions based on blocked polyisocyanates which are deblocked during stoving;

4. two-component paint or varnish compositions based on (poly)ketimines and aliphatic or aromatic polyisocyanates;

5. two-component paint or varnish compositions based on (poly)ketimines and an unsaturated acrylate resin or a polyacetoacetate resin or a methyl acrylamidoglycolate methyl ester;

6. two-component paint or varnish compositions based on carboxyl or amino group containing polyacrylates and polyepoxides;

7. two-component paint or varnish compositions based on anhydride group containing acrylate resins ad a polyhydroxy or polyamino component;

8. two-component paint or varnish compositions based on (poly)oxazolidines and anhydride group containing acrylate resins or unsaturated acrylate resins or aliphatic or aromatic polyisocyanates;

9. two-component paint or varnish compositions based on unsaturated polyacrylates and polymalonates;

10. thermoplastic polyacrylate paint or varnish compositions based on thermoplastic acrylate resins or not self-crosslinking acrylate resins in conjunction with etherified melamine resins;

11. paint or varnish systems based on siloxane-modified acrylate resins; and 12. paint or varnish systems based on fluorine-modified acrylate resins.

The paint or varnish compositions may also be photocurable compositions, in which case the binder consists of monomer or oligomer compounds which contain ethylenic double bonds and which are converted by actinic light or with electron beams into a crosslinked high molecular weight form. The binder is usually a mixture of such compounds.

The paint or varnish compositions may be applied as single layer or two-layer systems, in which case the stabilisers of this invention are preferably added to the topmost layer.

The paint or varnish compositions can be applied to the substrates (metal, plastic, wood and the like) by the conventional techniques, for example by brushing, spraying, coating, immersion or electrophoresis.

Paint or varnish compositions which are applied to motor cars (automotive lacquers) are especially preferred.

Provided the light-sensitive organic materials of this invention are paint or varnish composition, these latter will preferably contain no alkyd resins as binders.

The compounds of formula (1) may be incorporated in the paint or varnish compositions as well as other light-sensitive organic materials by conventional known methods. The amounts are usually in the range from 0.01 to 5.0% by weight, preferably from 0.02 to 3.0% by weight, based on the organic material. The amount of UV absorber to be chosen will be dependent on the nature of the material and the requirements made of its stability.

The components of stabiliser combinations can be added singly or in admixture to the organic material. The addition of compounds of formula (1) and additional optional stabilisers is preferably made before or during the shaping of the material if it is, for example, a thermoplastic. The addition can, however, also be made during polymerisation or before polymerisation to the starting monomers.

The compounds of formula (1) can be prepared by methods which are known pe se, for example, by heating a mixture of the compounds of formulae

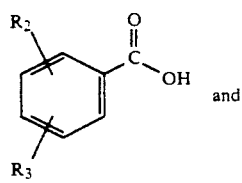

(2)

and

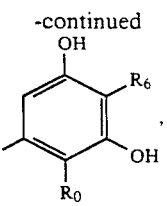

(3)

wherein $R_0$, $R_2$, $R_3$, $R_6$ and X have the given meanings, it is possible to obtain the intermediate of formula

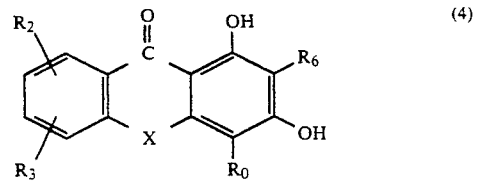

(4)

which, by reaction with, for example, $R_1$—Cl or $R_1$—Br, wherein $R_1$ has the given meaning, can be converted into the compound of formula (1).

The invention is illustrated in more detail by the following Examples in which parts and percentages are by weight, unless otherwise stated.

PREPARATORY EXAMPLES

Example 1

22.8 g of 1,3-dihydroxyxanthone (prepared according to Grover, J. Chem. Soc. 1955, 3982) together with 15.2 g of $K_2CO_3$ and 21.2 g of 1-bromooctane are refluxed for 15 hours in 250 ml of methyl ethyl ketone. The salt is isolated by filtration from the cooled reaction mixture and the methyl ethyl ketone solution is concentrated by evaporation under vacuum. Recrystallisation of the residue from heptane gives 1-hydroxy-3-octoxyxanthone with a melting point of 98° C.

Example 2

22.8 g of 1,3-dihydroxyxanthone (prepared according to Grover, J. Chem. Soc. 1955, 3982) are charged to 300 ml of absolute ethanol. Then 11.2 g of potassium tert-butylate, and afterwards 0.5 g of potassium iodide, are slowly added dropwise. Then 12.3 g of ethyl chloroacetate are added dropwise at room temperature over ca. 15 minutes and the reaction mixture is thereafter heated for 6 hours under reflux. The reaction mixture is poured into 500 ml of water and acidified with 200 ml of glacial acetic acid. The precipitate is isolated by filtration and dried. Recrystallisation from hexane gives the compound of formula

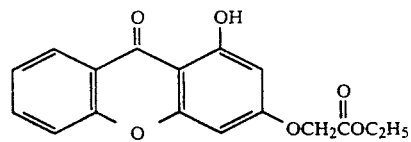

with a melting point of 165° C.

Example 3

22.8 g of 1,3-dihydroxyxanthone (prepared according to Grover, J. Chem. Soc. 1955, 3982) are heated in 200 ml of xylene to 120° C. After the addition of 1.5 g of tetrabutylammonium bromide, 20.5 g of 2-ethylhexyl glycidyl ether are added dropwise and the reaction mixture is thereafter stirred for 24 hours at 120° C. Then 5 g of Tonsil AC are added to the reaction solution, which is stirred for 5 minutes at 110° C. and clarified by filtration. The filtrate is concentrated by evaporation, the residue is taken up in 300 ml of hexane, and 50 g are filtered over silica gel. The filtrate is concentrated by evaporation to give the compound of formula

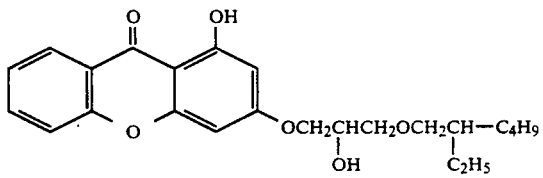

in the form of a yellowish resin which slowly crystallises. Melting point: 56°–58° C.

USE EXAMPLE 1

The UV absorbers of the invention are tested in a two-layer metallic paint.

A clear varnish of the following composition is prepared:

| | |
|---|---|
| Uracron ® 2263 XB (50%) | 59.2 parts |
| Cymel ® 327 (90%) | 11.6 parts |
| Baysilon ® A (1% in xylene) | 1.0 part |
| butyl glycol acetate | 5.5 parts |
| xylene | 19.4 parts |
| butanol | 3.3 parts |
| | 100.0 parts |

To the above composition is added a solution of 1 part of the compound of Example 1 in 10 parts of xylene.

This clear varnish composition is diluted with a mixture of xylene (13 parts), butanol (6 parts) and butyl glycol acetate (1 part) to a sprayable consistency and sprayed on to a prepared aluminium sheet (coil coated, automotive filler, silver metallic primer lacquer based on polyester/cellulose acetate butyrate/melamine resin) and stoved for 30 minutes at 130° C. The resultant finish has a dry layer thickness of 40 to 50 μm. For comparison purposes, a similarly prepared aluminium sheet is coated with the above clear varnish composition from which the UV absorbers are excluded.

The specimens so obtained are subjected to weathering and then tested for gloss retention. Compared with the specimen without UV absorber, the stabilised specimens exhibit a markedly better resistance to weathering. The results are reported in the following Table 1.

TABLE 1

Evaluation of gloss retention after weathering according to DIN 67 530 (20° C. gloss)

| | 20° gloss after | | | | |
|---|---|---|---|---|---|
| UV Absorber | 0 | 400 | 800 | 1200 | hours |
| none | 86 | 75 | 45 | 16 | |
| according to Example 1 | 84 | 78 | 74 | 81 | |
| according to Example 2 | 85 | 75 | 68 | 74 | |
| according to Example 3 | 86 | 80 | 80 | 80 | |
| according to | 85 | 73 | 70 | 74 | |

TABLE 1-continued

Evaluation of gloss retention after weathering according to DIN 67 530 (20° C. gloss)

| | 20° gloss after | | | | |
|---|---|---|---|---|---|
| UV Absorber | 0 | 400 | 800 | 1200 | hours |
| formula (5) | | | | | |

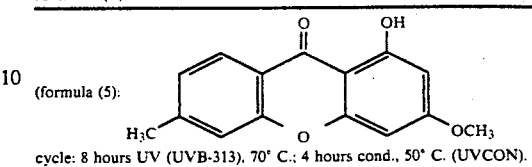

cycle: 8 hours UV (UVB-313), 70° C.; 4 hours cond., 50° C. (UVCON).

Use Example 2

The procedure of Use Example 1 is repeated, except that 0.5 part of the compound of formula (6)

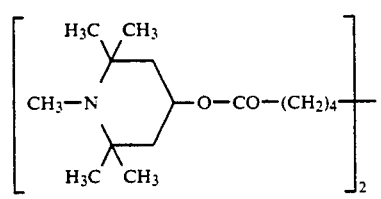

is additionally used. The results are reported in Table 2.

TABLE 2

Evaluation of gloss retention after weathering according to DIN 67 530 (20° C. gloss)

| | 20° gloss after | | | | |
|---|---|---|---|---|---|
| UV Absorber | 0 | 400 | 800 | 1200 | hours |
| none | 86 | 71 | 52 | 36 | |
| 1 part according to Example 1 + 0.5 part of (6) | 86 | 70 | 61 | 56 | |
| 1 part according to Example 3 + 0.5 part of (6) | 86 | 74 | 66 | 57 | | cycle: VDA method C (Xenotest 1200)

What is claimed is:
1. A compound of the formula

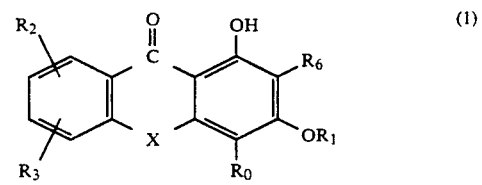

wherein X is O and $R_0$ is hydrogen or a radical of formula $-(CH_2)_nCO_2R$, wherein n is 1 or 2 and R is alkyl of 1 to 18 carbon atoms or $-(CH_2CH_2O)_mH$, wherein m is 1 to 12, $R_1$ is alkyl of 4 to 18 carbon atoms which is substituted by hydroxyl and interrupted by non-adjacent oxygen atoms, or is $-COR_4$, wherein $R_4$ is alkyl or alkenyl, each of 2 to 12 carbon atoms

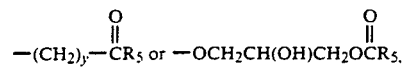

or $R_1$ is $$-(CH_2)_yO-\overset{\overset{O}{\|}}{C}R_5 \text{ or } -(CH_2)_y-\overset{\overset{O}{\|}}{C}OR_5.$$

wherein $R_5$ is alkyl of 1 to 12 carbon atoms or alkenyl of 2 to 12 carbon atoms, and y is 1 to 12, and $R_2$ and $R_3$ are each independently of the other hydrogen, alkyl of 1 to 12 carbon atoms, alkenyl of 2 to 12 carbon atoms, $-OR_1$, wherein $R_1$ has the given meaning, or are chloro, and $R_6$ is hydrogen or alkyl of 1 to 4 carbon atoms.

2. A compound according to claim 1, wherein $R_2$ and $R_3$ are hydrogen or methyl.

3. A compound according to claim 1, wherein $R_1$ is alkyl of 4 to 12 carbon atoms which may be substituted by hydroxyl and/or interrupted by oxygen, or is $-COR_4$ or $$-(CH_2)_y\overset{\overset{O}{\|}}{C}OR_5.$$

wherein $R_4$ is alkyl of 4 to 8 carbon atoms, y is 1 to 4, and $R_5$ is alkyl of 1 to 4 carbon atoms.

4. A compound according to claim 1, wherein $R_0$ is a radical of formula $-CH_2CH_2CO_2R$, wherein R is alkyl of 1 to 8 carbon atoms or $-CH_2CH_2O_mH$ and m is 6 to 8.

* * * * *